United States Patent [19]

D'Alerta

[11] Patent Number: 5,423,874
[45] Date of Patent: Jun. 13, 1995

[54] PATCH FOR APPLYING PAIN REDUCING ELECTRICAL ENERGY TO THE BODY

[76] Inventor: Mario D'Alerta, 137 SW. 136 Pl., Miami, Fla. 33184

[21] Appl. No.: 216,961

[22] Filed: Mar. 24, 1994

[51] Int. Cl.$^6$ .............................................. A61N 1/36
[52] U.S. Cl. .......................................... 607/72; 607/46
[58] Field of Search ......................... 607/46, 50, 51, 72

[56] References Cited

U.S. PATENT DOCUMENTS

| | | |
|---|---|---|
| 4,398,545 | 8/1983 | Wilson . |
| 4,841,966 | 6/1989 | Hagen et al. . |
| 4,895,153 | 1/1990 | Takeuchi et al. . |
| 4,922,906 | 5/1990 | Takeuchi et al. . |
| 4,982,742 | 1/1991 | Claude . |
| 5,085,217 | 2/1992 | Shimizu . |
| 5,158,081 | 10/1992 | McWhorter et al. . |
| 5,169,384 | 12/1992 | Bosniak et al. . |

Primary Examiner—William E. Kamm
Attorney, Agent, or Firm—Jacobson, Price, Holman & Stern

[57] ABSTRACT

An electronic patch device which attaches to the surface of the body for preventing nerves from transmitting "pain" information to the brain. The device has a slim profile and comprises a circuit layer which supports an electronic circuit, a double sided adhesive layer, a top layer which seals the circuit layer from moisture and a backing layer. A cathode and an anode are disposed in apertures of the adhesive layer and make electrical contact with respective pins of the electronic circuit in the circuit layer. On opposite surfaces the cathode and anode are exposed to make contact with the skin of a patient when the backing layer is removed.

9 Claims, 4 Drawing Sheets

PATCH FOR APPLYING PAIN REDUCING ELECTRICAL ENERGY TO THE BODY

BACKGROUND OF THE INVENTION

The present invention relates to a device having an electronic circuit incorporated therein for generating and delivering electrical energy through an afflicted region on a patient's body.

Delivering electrical energy in controlled energy levels to the body of a patient is known to be useful in treating body pain, and particularly inflammation in muscles and bones. Specifically, electronic energy delivered at a certain frequency causes a reduction in the ability of a nerve to transmit information to the brain, such as pain. Temporary and sometimes permanent relief can be achieved. In some instances, the electrically energy is ideally delivered non-invasively.

To this end, efforts have been made to design devices for applying electrical energy to the body of a patient. See, for example, U.S. Pat. Nos. 4,398,545 to Wilson; 4,982,742 to Claude; 5,169,384 to Bonsiak et al.; 4,895,153 and 4,922,906 to Takeuchi et al.; 5,158,081 to McWhorter et al.; 4,841,966 to Hagen et al.; and 5,085,217 to Shimizu.

The Claude and Wilson patents are representative of prior devices which are bandage type devices that include "on-board" circuitry for generating and delivering electrical energy to the region to which the bandage is attached. However, these prior designs are inadequate insofar as they have bulky designs which cannot sufficiently conform to the surface of a patient's body.

SUMMARY OF THE INVENTION

It is a primary object of the present invention to provide an electronic patch device which has a slim profile.

It is a further object of the present invention to provide a device to apply electrical energy to the body which flexibly attaches to the surface of the body.

Briefly, the present invention is directed to an electronic patch device which attaches to the surface of the body. The device has a slim profile and comprises a circuit layer which supports an electronic circuit, a double sided adhesive layer, a top layer which seals the circuit layer from moisture and a backing layer. A cathode and an anode are disposed in apertures of the adhesive layer and make electrical contact with respective pins of the electronic circuit in the circuit layer. The cathode and anode are exposed to make contact with the skin of a patient when the backing layer is removed.

The top layer has a generally dome profile and a further small dome-shaped cap is provided in the center of the top layer. This cap is aligned with a switch used for activating the electronic circuit. The electronic circuit includes a battery, timer, LED and transformer. A series of spaced pulses are generated by the electronic circuit and conveyed to the cathode and anode.

The above and other objects, advantages and modifications will become readily apparent when reference is made to the following description taken in conjunction with the accompanying drawings.

DETAILED DESCRIPTION OF THE DRAWINGS

Figure 1:
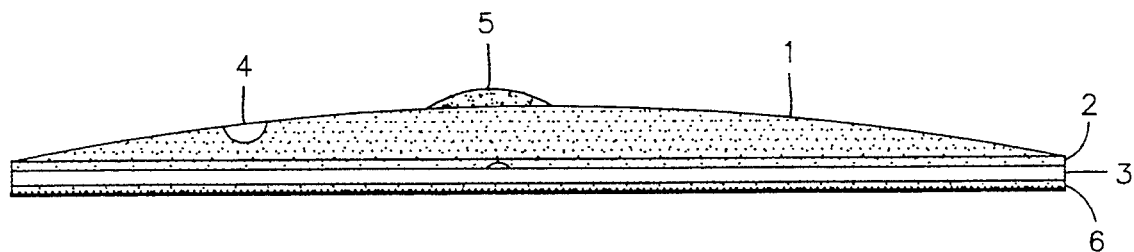
FIG. 1 is a side profile of the electronic patch device in accordance with the present invention.
Figure 2:
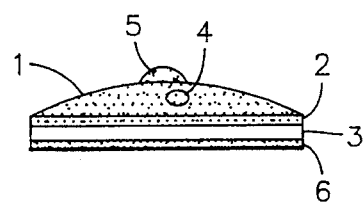
FIG. 2 is a front end view of the electronic patch device.
Figure 3:
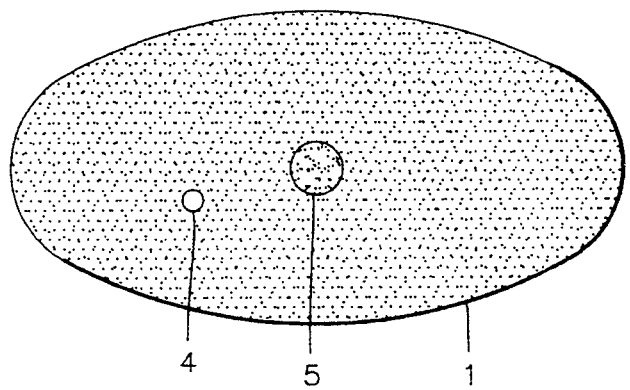
FIG. 3 is a top view of the electronic patch device.

Referring first to FIGS. 1–5, the electronic patch device comprises an impermeable top layer 1, a circuit layer 2, an intermediate double sided adhesive layer 3 and an adhesive backing layer 6. The top layer 1 has a slightly curved or dome-shaped profile as shown in FIG. 1 and is made of impermeable material to seal the circuit layer 2 from moisture. A window 4 is provided in the top layer 1, to receive an LED which will be described in more detail hereinafter. In addition, a small dome-shaped cap 5 is provided on the top layer 1 which encloses an activation switch, to be described hereinafter. As shown in FIG. 1, the electronic patch has a curved profile such that it is thicker at the center of the body and gradually thinner towards the periphery.

Figure 4:
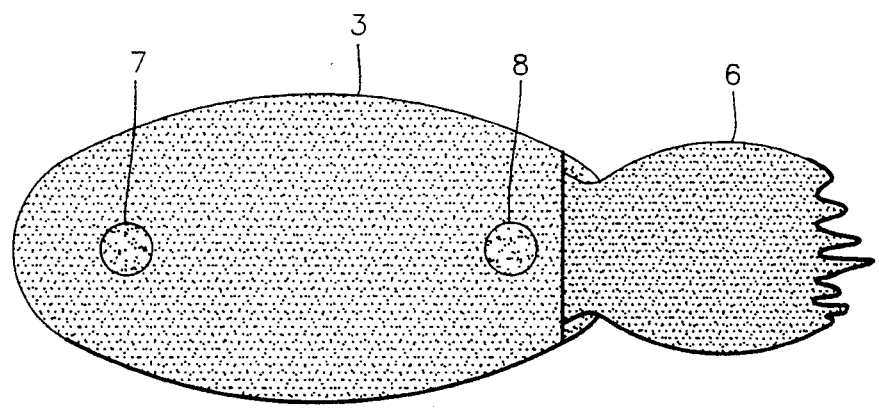
FIG. 4 is a bottom view of the electronic patch device and illustrating the partially removed peel-away backing.
Figure 5:
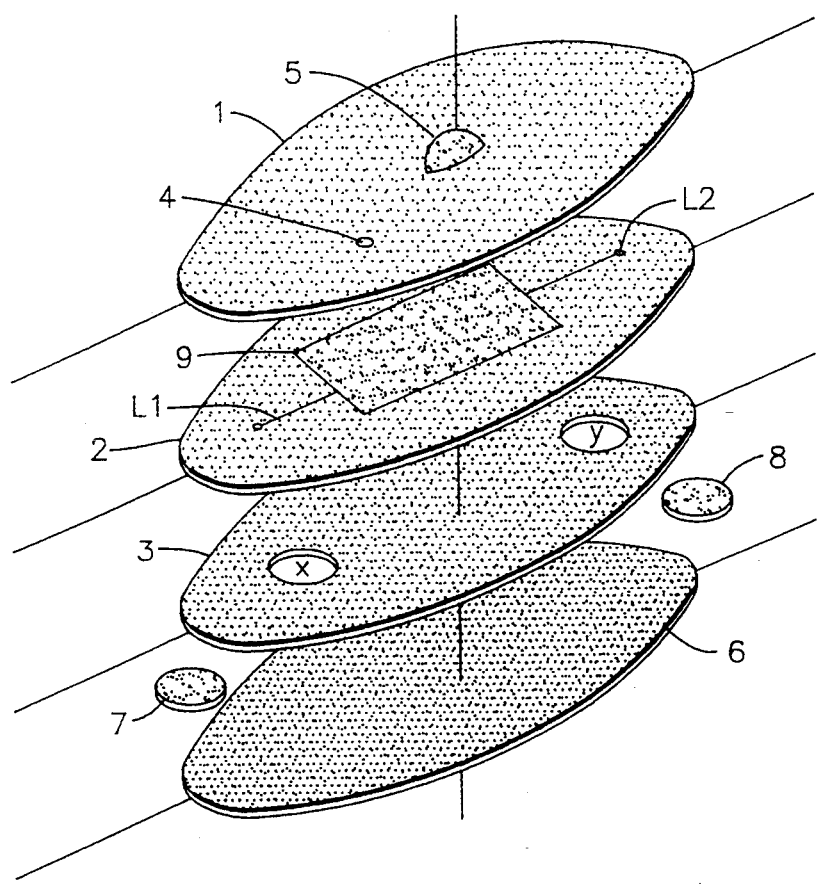
FIG. 5 is a perspective disassembled view showing the various layers of the electronic patch device.

The intermediate adhesive layer 3 is a thin double-sided adhesive foam pad. As shown in FIG. 4 and 5, the intermediate adhesive layer comprises two apertures, labelled X and Y, which are provided to retain a cathode 7 and an anode 8, respectively. The cathode 7 and anode 8 are treated with a conductive gel on their exposed surfaces prior to packaging to provide for better conductivity of current to the afflicted region. The cathode 7 and anode 8 are exposed at the bottom of the adhesive layer, and are designed to lie slightly below the surface of adhesive layer 3 to readily make contact with the skin of a patient. Moreover, the cathode 7 and anode 8, when retained in the adhesive layer 3, make electrical contact with leads L1 and L2, respectively, of the electronic circuit 9. See also FIGS. 6A and 6B.

The backing layer 6 is preferably made of thin, flexible aluminum to protect the circuit 9 from accidental static discharge.

Figure 6A:
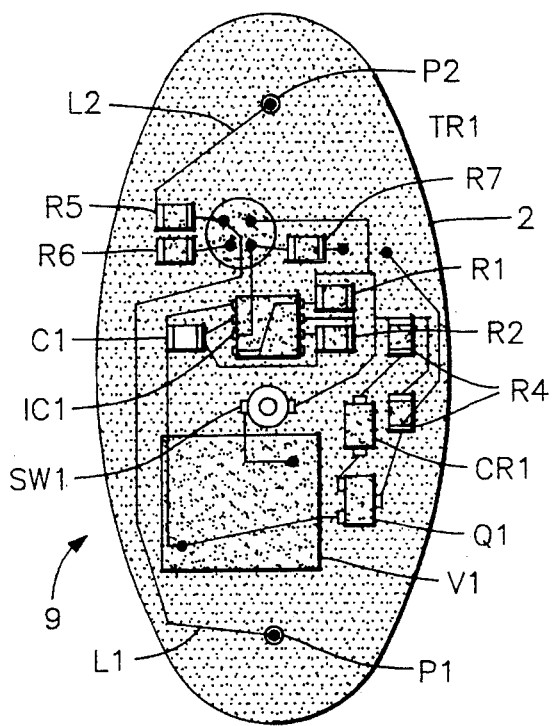
FIG. 6A is a top view of the circuit layer, and showing the electronic components.
Figure 6B:
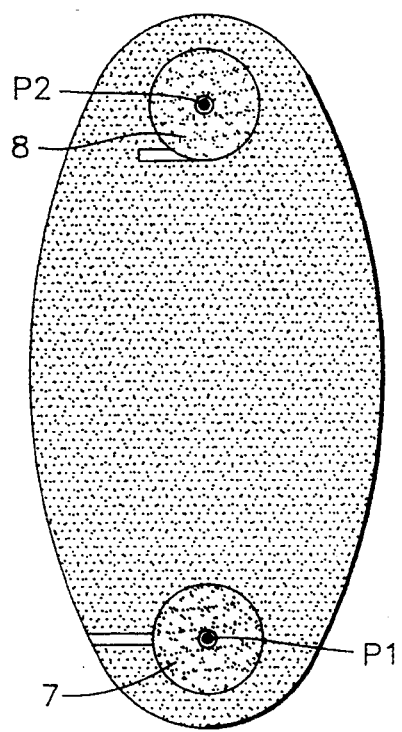
FIG. 6B is a bottom view of the circuit layer, and showing the exposed cathode and anode.

FIGS. 6A and 6B illustrate the circuit layer 2 in greater detail. The electronic circuit 9 comprises components which are "surface mounted". That is, the pins or contacts of the components are soldered on the same side of the circuit layer; the solder connection is not made on the bottom side. The surface mounted components are resistors R1, R2, R3, R5, R6, R7; capacitor C1; LED CR1; integrated circuit IC1 and FET transistor Q1. A micro-switch SW1 is provided to activate and de-activate the device. Miniature transformer TR1 generates sufficient voltage and current to drive cathode 7 and anode 8. Leads L1 and L2 are connected to pins P1 and P2, respectively, which make contact with the cathode 7 and anode 8, respectively. The LED CR1 is oriented on the circuit layer 2 in alignment with the window 4 of the top layer. Orientation of the switch SW1 relative to the cap 5 is shown in greater detail in FIGS. 10A and 10B.

Cathode 7 and anode 8 are made of electrically conductive material and are approximately 0.5 inch in diameter. The cathode and anode are placed beneath the circuit layer and soldered to their respective contacts.

Figure 7:
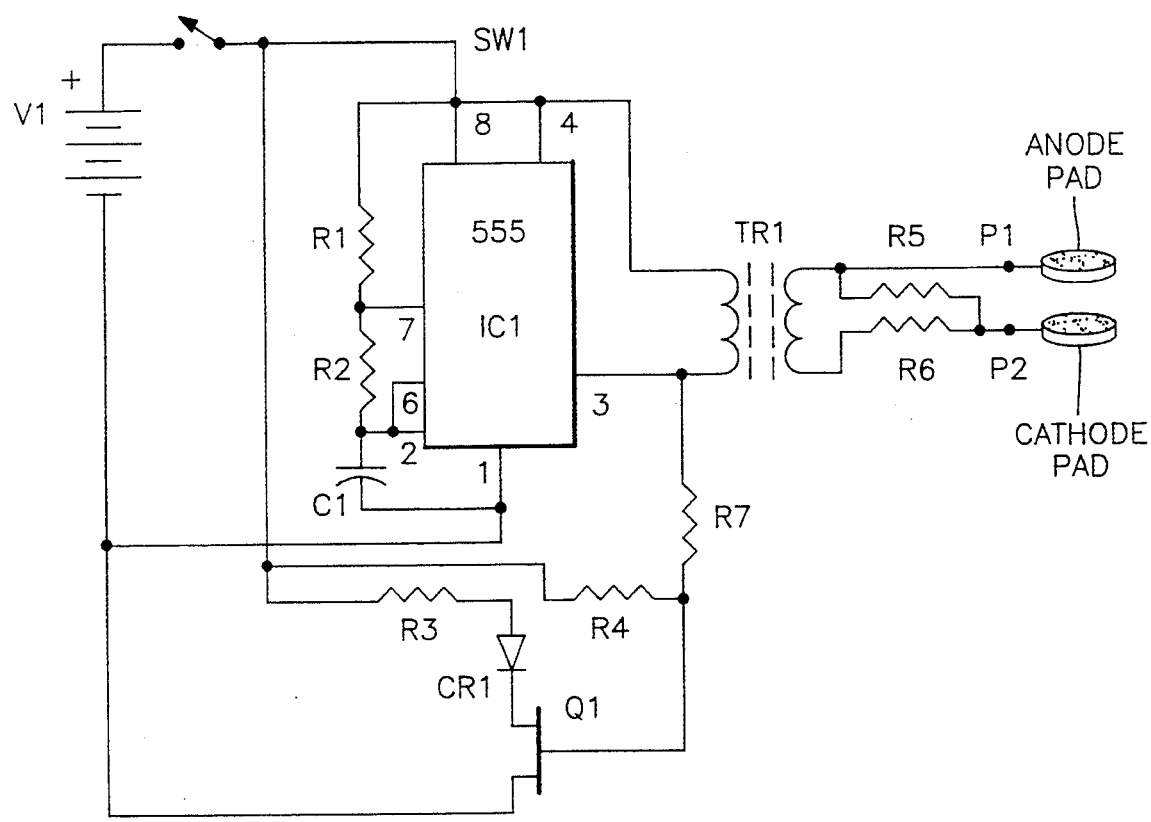
FIG. 7 is a schematic diagram of the electronic circuit in accordance with the present invention.

Turning to FIG. 7, the electronic circuit 9 will be described. A battery is represented by V1. IC1 provides a constant time base for the current burst delivered to the skin region. The time base may be changed by increasing the values of R1, R2 and C1. For best results, R1 should be 47K Ohms, R2 should be 1K Ohms and C1 should be 0.1 microfarads.

The output on pin 3 of timer IC1 is directly coupled to transformer TR1 which steps up the voltage to approximately 50 volts DC. Pin 3 is also used to trigger actuation of the LED CR1. The transformer has a step-up ratio of about 1 to 100. Resistors R5 and R6 are used as a voltage divider to provide precise voltage to the cathode via pin P2 and anode via pin P1. Resistors R4 and R7 are bias resistors for FET transistor Q1. Transistor Q1 drives LED CR1 when conducting. The power consumption of LED CR1 is limited by resistor R3. Switch SW1 controls the activation of the circuit, as will be described in conjunction with FIGS. 10A and 10B.

Figure 8:
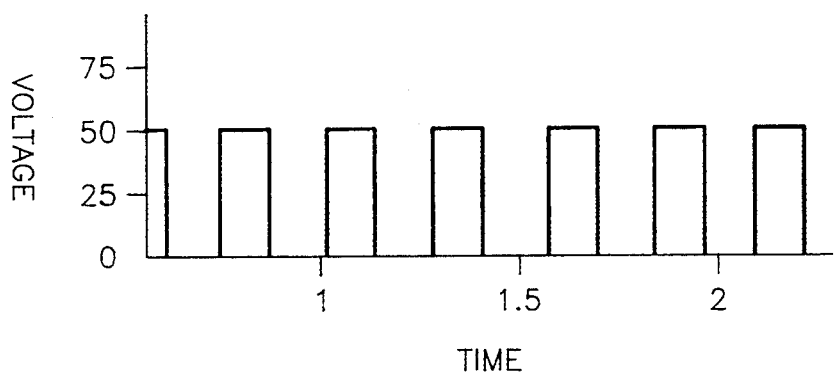
FIG. 8 is a waveform diagram illustrating the output of the electronic circuit at the anode and cathode.

In FIG. 8, the waveform of voltage applied between the cathode 7 and anode 8 is illustrated. The current and voltage are in phase and are sustained at a level greater than zero for a short period of time, in repeated pulses or bursts. A 50% duty cycle waveform is created comprising a series of spaced 50 volt pulses with a period of 0.25 to 2 seconds. Longer periods allow for less bursts to be applied to the area, decreasing patient discomfort. Further, each pulse has a significant duration, as illustrated. The actual waveform may be somewhat conical in shape.

Figure 9:
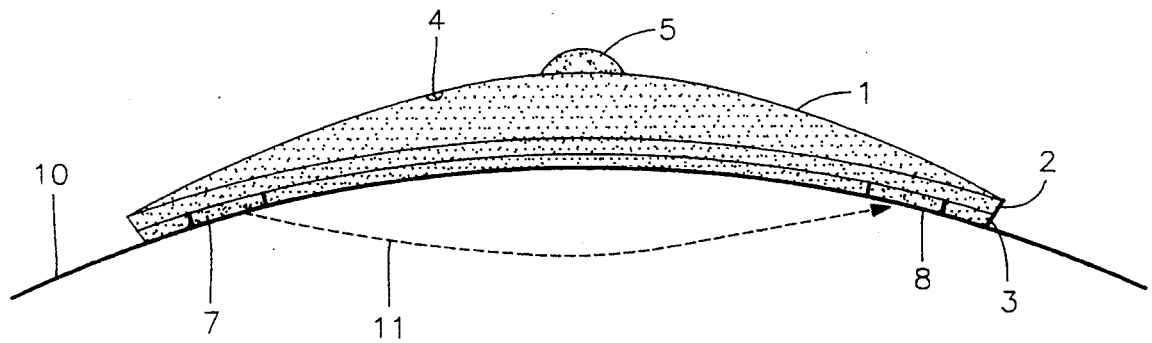
FIG. 9 is a side view of the electronic patch device as it is attached to the skin of a patient.

FIG. 9 illustrates the profile of the patch when attached to the skin 10 of a patient. As shown in the figure, the patch device has a curved profile and is very flexible to conform to curved skin surfaces. Current flow from the cathode 7 through the patient to the anode 8 is depicted by the dotted line 11.

Figure 10A:
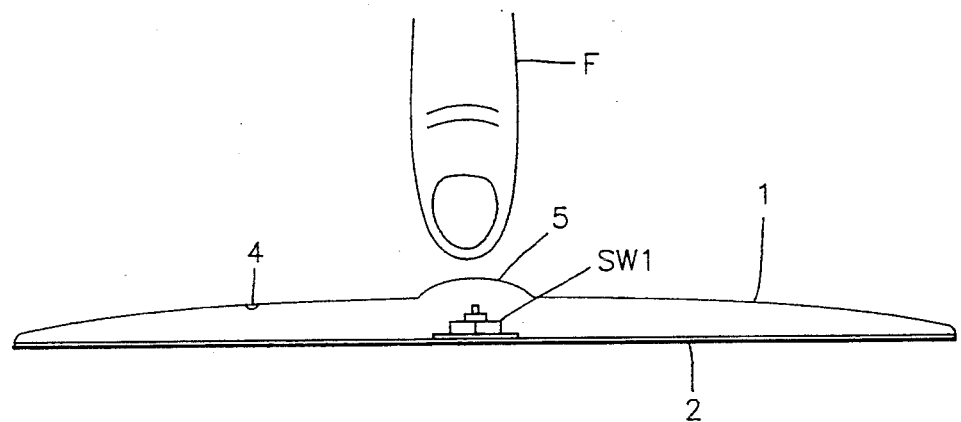
FIG. 10A is a side view of the electronic patch device prior to depressing the activation switch.
Figure 10B:
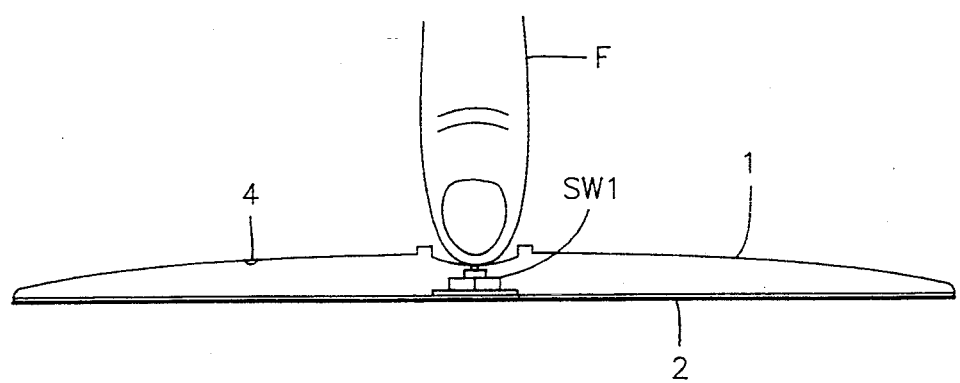
FIG. 10B is a side view showing the profile of the electronic patch device after depressing the switch.

Turning now to FIGS. 10A and 10B, the switch SW1 is aligned with the cap 5. Cap 5 is dome-shaped and deformable. By depressing the cap 5, SW1 may be activated as shown in FIG. 10B.

In operation, when the switch SW1 is activated, the LED CR1 blinks, indicating that the current bursts (FIG. 8) are being delivered through the patient. If the LED does not blink when the switch SW1 is depressed, this signifies that the battery of the patch is expired and the patch may be discarded.

Unlike any prior art device heretofore known, the electronic patch device according to the present invention is a slim profile device. In addition, the oval shape of the patch device allows it to be placed in areas of the body where rectangular bandages are ineffective. Moreover, the patch device is made of flexible material, and owing also to its oval shape, is able to conform to the topology of the patient's body, ensuring that the cathode and anode make contact with the patient's skin. The device may be disposed of when the battery is depleted. Indeed, the failure of the LED to illuminate when switch SW1 is depressed indicates depletion of the battery.

The electronic patch device according to the present invention is used to treat pain caused by inflammation in muscles and bones by preventing nerves from transmitting "pain" information to the brain. It also finds utility in the treatment of a number of afflictions such as arthritis, tendinitis, rheumatism, migraines and others.

The above description is intended by way of example only and is not intended to limit the present invention in any way except as set forth in the following claims.

What is claimed is:

1. An electronic patch device for attachment to the skin of a patient and for applying electrical energy to a region where the patch device is attached, the electronic patch device comprising:
   an oval shaped patch body comprising:
      a top layer which is impermeable to liquids;
      a circuit layer supporting an electronic circuit for generating pulses of electrical energy;
      an intermediate layer having adhesive on top and bottom surfaces, and having first and second apertures located on opposite ends thereof;
      a cathode and an anode retained in said first and second apertures of said intermediate layer and connected to said electronic circuit; and
      an adhesive backing layer attached to the bottom side of the intermediate layer, which when removed exposes the adhesive bottom surface of said intermediate layer and said cathode and anode.

2. The electronic patch device of claim 1, and wherein said electronic circuit further comprises switch means for triggering the generation of electrical pulses, said switch means being disposed on said circuit layer and protruding slightly therefrom, said top layer further comprising a small dome-shaped cap aligned with said switch means and said cap being deformable so as to allow a user to activate said switch by depressing said cap.

3. The electronic patch device of claim 1, wherein said electronic circuit further comprises an LED which is activated to blink when said electronic circuit generates and delivers electronic pulses, said top player further comprising a small window aligned with said LED.

4. The electronic patch device of claim 1, wherein said circuit layer comprises first and second electrically conductive pins connected to respective lead lines dedicated for the cathode and anode, respectively, and wherein said pins make electrical contact with said first and second cathode and anode, respectively.

5. The electronic patch device of claim 1, wherein said electronic circuit generates a series of spaced pulses of predetermined duration.

6. The electronic patch device of claim 1, wherein said electronic circuit comprises switch means, battery means, timer means connected to said battery means via said switch means, and transformer means connected to the output of said timer means for stepping up the voltage thereof for delivery to the cathode and anode.

7. The electronic patch device of claim 6, wherein said electronic circuit further comprises an LED connected to said switch and which is responsive to said battery means when said switch closes to illuminate.

8. The electronic patch device of claim 1, wherein said bandage body has a curved profile such that it is thicker at the center of the body and gradually thinner towards the periphery.

9. The electronic patch device of claim 1, wherein the apertures in the intermediate adhesive layer are positioned at opposite ends of its oval shape.

* * * * *